United States Patent [19]
DaPrato et al.

[11] Patent Number: 5,689,073
[45] Date of Patent: Nov. 18, 1997

[54] VERIFICATION CIRCUIT FOR A FLUID HANDLING ANALYTICAL INSTRUMENT

[75] Inventors: Larry J. DaPrato, Cincinnati; Michael A. Hill, Loveland, both of Ohio

[73] Assignee: Tekmar Company, Cincinnati, Ohio

[21] Appl. No.: 556,661

[22] Filed: Nov. 13, 1995

[51] Int. Cl.$^6$ .................................................. G01N 1/16
[52] U.S. Cl. ........................................ 73/863.01; 73/863.12
[58] Field of Search ........................... 73/863.01, 863.11, 73/863.12, 864.81, 863.02, 863.03, 863.86, 864.24, 864.25

[56] References Cited

U.S. PATENT DOCUMENTS

| | | | |
|---|---|---|---|
| 4,165,643 | 8/1979 | Moll et al. | 73/863.11 |
| 4,756,186 | 7/1988 | Sangawa | 73/119 A |

*Primary Examiner*—Robert Raevis
*Attorney, Agent, or Firm*—Westman, Champlin & Kelly, P.A.

[57] ABSTRACT

A fluid handling analytical instrument includes a controlled device and a controller operably coupled to the controlled device to selectively control the controlled device with a control signal. A sensing device is operably coupled to the controller to sense the control signal and provide a signal indicative of a status of the control signal.

12 Claims, 5 Drawing Sheets

VERIFICATION CIRCUIT FOR A FLUID HANDLING ANALYTICAL INSTRUMENT

BACKGROUND OF THE INVENTION

The present invention relates to fluid handling analytical instruments. More particularly, the present invention relates to a means for verifying the operational status of components of the fluid handling analytical instrument.

SUMMARY OF THE INVENTION

A fluid handling analytical instrument includes a controlled device and a controller operably coupled to the controlled device to selectively control the controlled device with a control signal. A sensing device is operably coupled to the controller to sense the control signal and provide a signal indicative of a status of the control signal.

DETAILED DESCRIPTION OF THE PREFERRED EMBODIMENTS

Figure 1:
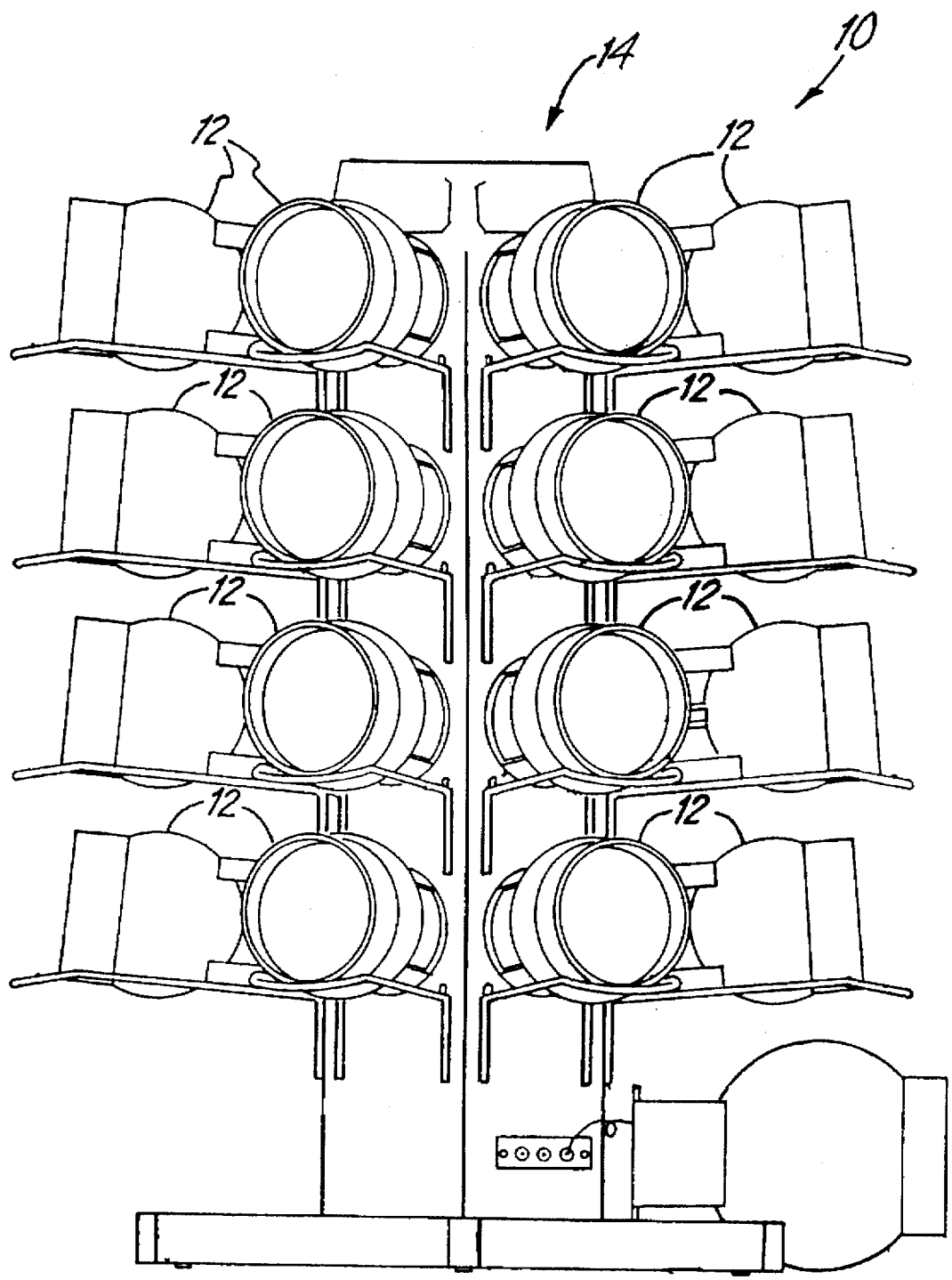
FIG. 1 is a front elevational view of a fluid sampling system.

An exemplary fluid handling analytical instrument is illustrated in FIG. 1 generally at 10 as a fluid sampling system. The fluid sampling system 10 allows random, controlled access of the contents of sample enclosures 12. As used herein, the word "sample enclosure" includes any standard gas collection or fluid collection container such as a standard stainless steel canister (e.g. SUMMA), bags (e.g. TEDLAR), glass bottles, tubes and the like for holding fluids in either a gaseous or liquid state.

Figure 2:
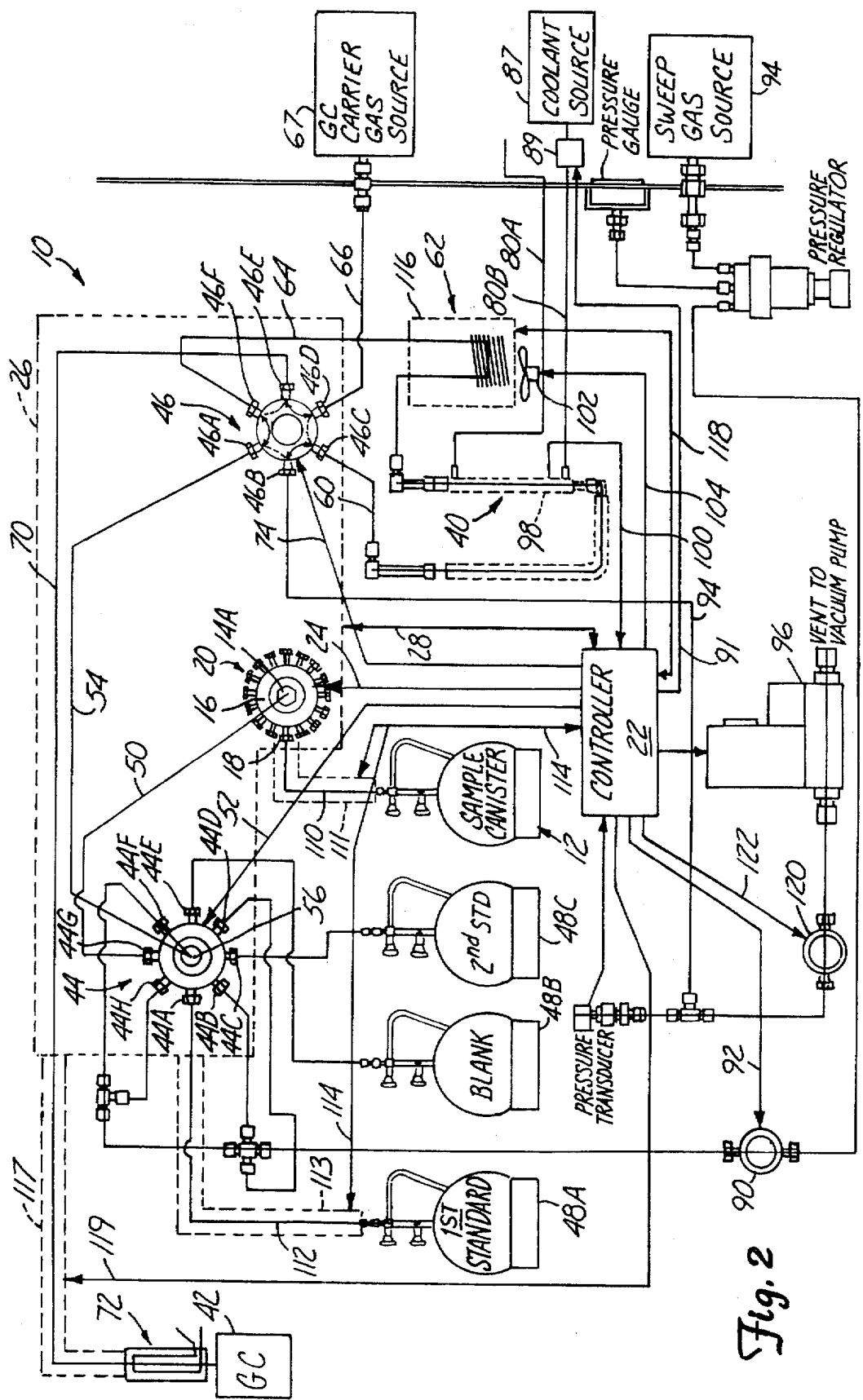
FIG. 2 is a schematic representation of the fluid sampling system illustrating fluid flow and control signal flow.

In the embodiment illustrated in FIG. 1, canisters 12 are depicted. The system can include a suitable stand 14 for supporting each of the canisters 12 at spaced-apart locations. Referring to FIG. 2, each of the canisters 12 are fluidly coupled to a multiposition valve 16. In FIG. 2, only one canister 12 is illustrated as being fluidly coupled to the multiposition valve 16 at an input port 18. It should be understood that the remaining input ports, generally designated at 20, can be individually fluidly coupled to other canisters 12.

A controller 22 operates the multiposition valve 16 by providing suitable control signals on a signal line 24. Preferably, the multiposition valve 16 is heated in the conventional manner (using a metal ring heated by a cartridge heater) and disposed in an insulated enclosure generally designated at 26 to avoid contamination (hereinafter "oven"). The controller 22 controls the oven 26 via a signal line 28 so as to maintain the multiposition valve 16 at a desired temperature. The oven 26 can include a conventional thermocouple to sense the temperature of the multiposition valve 16 directly, or by monitoring the temperature of the oven 26. A signal indicative of the temperature of the multiposition valve 16 is provided back to the controller 22 on signal line 28. As will be explained in detail below, the system 10 includes means for verifying the control signals are being provided to controlled devices such as the oven 26 in order to ensure proper operation of the system 10. Preferably, the controller 22 will ascertain if control signals are being properly sent immediately after power has been applied to the system 10. Verification that the fluid sampling system 10 is capable of operating as required by selectively activating each of the controlled devices found therein, ensures that the fluid sampling system 10 will operate correctly when samples are taken and analysis is performed.

Before describing the means for verifying in detail, a brief description of the fluid sampling system 10 illustrated in FIG. 2 will be helpful. It should be understood that the fluid sampling system 10 embodied in FIG. 2 is but one embodiment and includes many additional devices not generally needed to obtain samples from canisters 12. The fluid sampling system 10 embodied in FIG. 2, however, does provide illustrative examples of various devices that can be monitored. A complete description of the fluid sampling system 10 embodied in FIG. 2 is provided in co-pending application entitled AIR SAMPLER WITH TRAP, filed on the same date as the present application, the description of which is incorporated herein by reference.

Generally, the fluid sampling system 10 embodied in FIG. 2 obtains samples from any of the canisters 12 and collects selected compounds such as volatile organic compounds (VOCs) in a sorbent trap indicated at 40. The collected selected compounds from the sorbent trap 40 are then desorbed from the sorbent trap 40 and transferred to an analytical instrument such as a gas chromatograph (GC) and/or a mass spectrometer (MS) 42 where the quantities of the selected compounds are ascertained. The controller 22 communicates with the gas chromatograph 42.

The multiposition valve 16, a second multiposition valve 44, and a third multiposition valve 46 fluidly couple the canisters 12, and one or more canisters 48A, 48B and 48C, containing reference standards of known composition with the sorbent trap 40 and the gas chromatograph 42. As illustrated, the multiposition valve 44 is fluidly coupled to each of the reference standards 48A-48C at input ports 44A, 44C and 44E, respectively. A fluid flow line 50 couples an outlet port 14A of the multiposition valve 16 and an inlet port 44G of the multiposition valve 44. The controller 22 provides control signals to the multiposition valve 16 along signal line 24 and to the multiposition valve 44 along a signal line 52 to select any one of the reference standards 48A-48C or any one of the canisters 12.

A fluid flow line 54 fluidly couples an outlet port 56 of the multiposition valve 44 to an inlet port 46A of the multiposition valve 46. As illustrated, the multiposition valve 46 has six ports wherein each port is selectively fluidly connected separately to either of its adjacent ports. A first position is illustrated with solid lines and a second position is illustrated with dashed lines. A fluid flow line 60 fluidly couples a port 46C of the multiposition valve 46 to an end of the sorbent trap 40. The other end of the sorbent trap 40 is fluidly coupled through a known moisture control system indicated at 62 and through a fluid flow line 64 to a port 46F of the multiposition valve 46. A fluid flow line 66 couples a source of carrier gas 67 suitable for use with the gas chromatograph 42 to a port 46D of the multiposition valve 46. A fluid flow line 70 fluidly couples a port 46E of the multiposition valve 46 to the gas chromatograph 42. As illustrated, an optional cryofocusing module 72 can be fluidly coupled between fluid flow line 70 and the gas chromatograph 42.

In operation, the controller 22 provides suitable control signals to the multiposition valve 16, to the multiposition valve 44, and to the multiposition valve 46 along a signal line 74 to fluidly couple the sorbent trap 40 to the reference standards 48A–48C and any one of the canisters 12. The sorbent trap 40 receives cooling fluid such as liquid nitrogen through cooling lines 80A and 80B to cool the sorbent trap 40, and thus, collect selected compounds. After the selected compounds have been concentrated in the sorbent trap 40, the controller 22 operates the multiposition valve 44 and a valve 90 via a signal line 92 to allow sweep gas to flow from a suitable sweep gas source 94, through one of the inlet ports 44B, 44D, 44F and 44H, through the valve 46 (operated in the position illustrated with solid lines), through the sorbent trap 40 and out through a fluid flow line 94 to a mass flow controller 96. This step is called "dry purge" because moisture and other selected compounds are removed from the trap 40. Prior to or during the dry purge step, the controller 22 activates a heater 98 via a signal line 100 to heat the sorbent trap 40 to an intermediate temperature. After the dry purge step, the temperature of the sorbent trap 40 is elevated and the controller 22 operates the multiposition valve 46 to the position illustrated with dashed lines in order that carrier gas carries the selected compounds, typically VOCs, from the sorbent trap 40 and to the gas chromatograph 42 via the fluid flow line 70 during a "desorb" step.

Multiposition valves 44 and 46 are separately heated and disposed in the oven 26. In the preferred embodiment, a heater 111 heats the inlet lines 110 for the canisters 12 and heaters, such as that depicted at 113, heat the inlet lines for the reference standards 48A–48C. The controller 22 controls the inlet line heaters 111 and 113 through a signal line 114. The moisture control system 62 also includes a heater 116 which is controlled by the controller 22 through a signal line 118 while a heater 117 heats a portion of the transfer line 70 not within the oven 26. The controller 22 controls the heater 117 via a signal line 119. In addition, the controller 22 controls a solenoid actuated pressure lock valve 120 through a signal line 122.

Figure 3A:
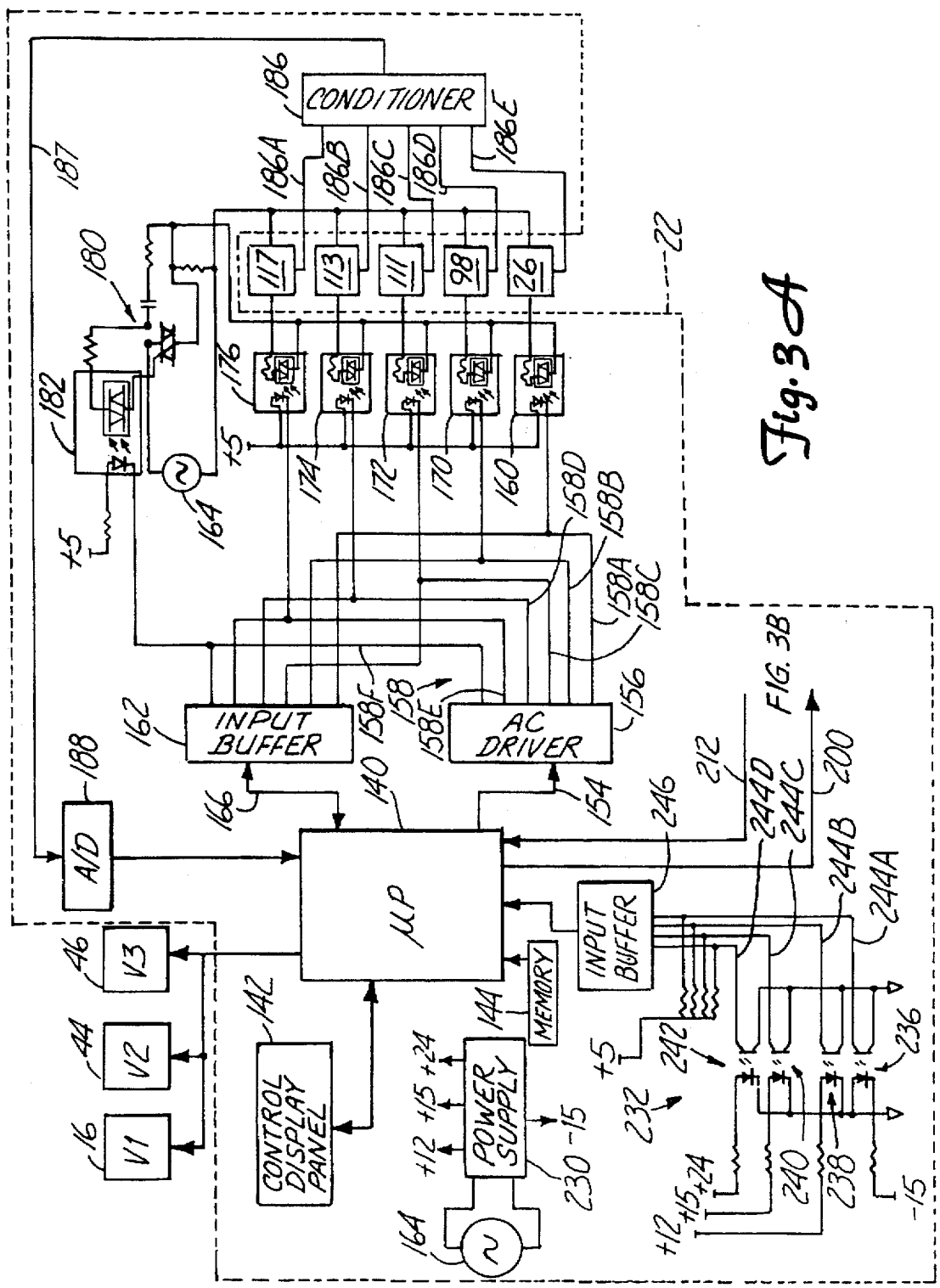
FIG. 3A-3B are block and circuit diagrams for the fluid sampling system.
Figure 3B:
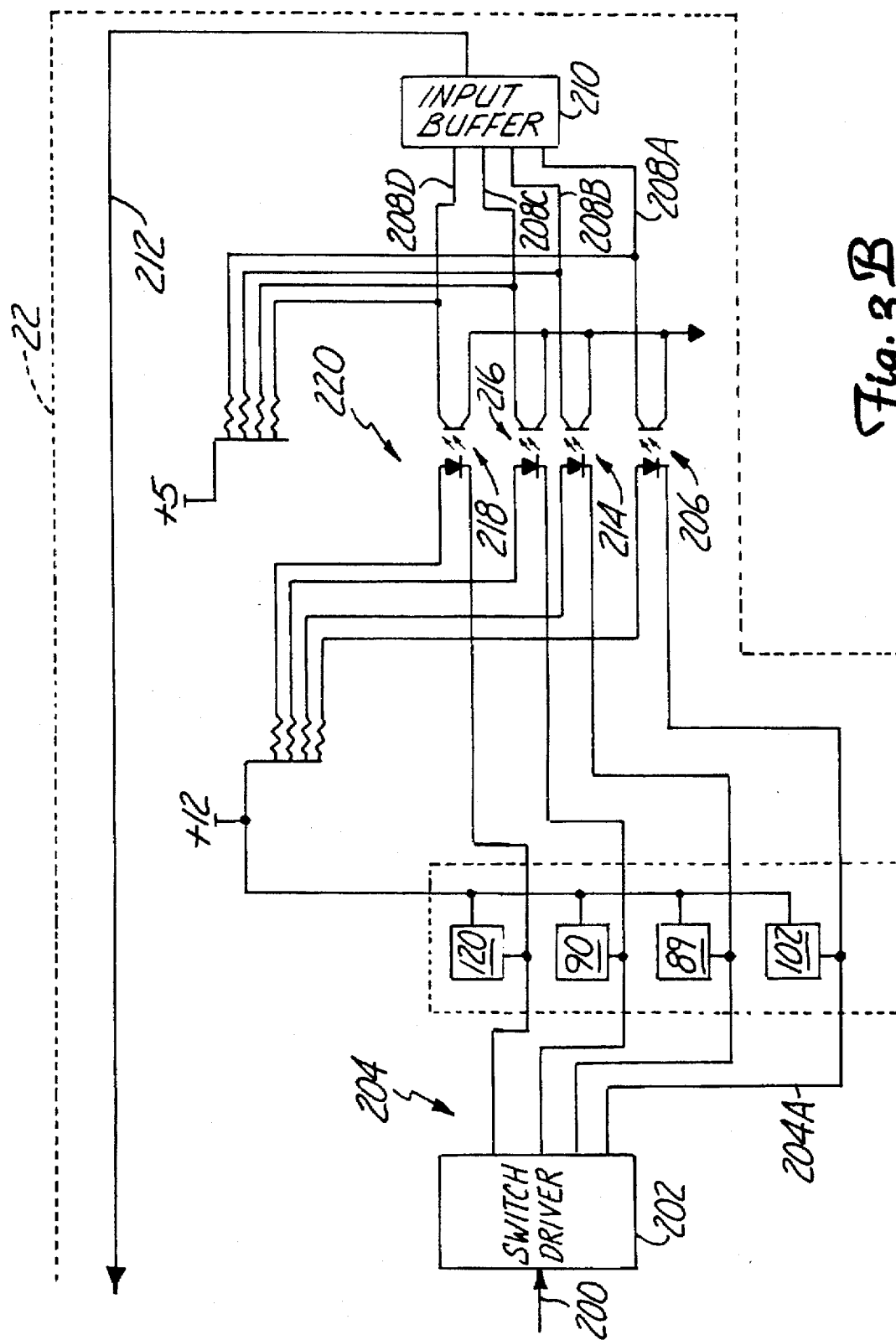

FIGS. 3A–3B illustrate a preferred embodiment of the controller 22. Multiposition valves 16, 44 and 46 and the heaters 98, 111, 113, 117, and those for oven 26 are schematically illustrated in FIG. 3A, while solenoid actuated valves 89, 90, 120 and fan 102 are shown schematically in FIG. 3B.

Referring back to FIG. 3A, the controller 22 includes a microprocessor 140 that receives signals from a control/display panel 142 and a suitable memory 144. Using a program stored in the memory 144, the microprocessor 140 verifies that control signals are being sent to each of the controlled devices such as the heaters 98, 111, 113, 117 and oven 26, and the solenoid actuated valves 89, 90, 120 and the fan 102.

The microprocessor 140 initiates or controls any one of the heaters 98, 111, 113, 117, or those in oven 26, providing a suitable control signal on a signal line 154 to an AC driver decoder indicated at 156. The AC driver decoder 156 includes a plurality of output control lines 158, which in an "unselected" condition are at approximately 5 volts DC. An output control line 158A is electrically coupled to a triac indicated at 160 and an input buffer indicated at 162. When a voltage potential of the control line 158A is lowered so as to activate the triac 160, electrical power is supplied from an alternating current power source 164 through the triac 160 to heaters in oven 26. Since the input buffer 162 is also electrically coupled to the control line 158A, the microprocessor 140 can access the input buffer 162 on a signal line 166 to ascertain if the control signal sent on signal line 154 was properly processed by the AC driver decoder 156 to lower the potential on the control line 158A. As illustrated, electrical power is also supplied to each of the heaters 98, 111, 113 and 117, through triacs 170, 172, 174 and 176, respectively. Voltages on control lines 158B, 158C, 158C and 158E are lowered and raised similar to control line 158A, described above, to activate the triacs 170, 172, 174 and 176. The input buffer 162 also monitors the voltage potentials on the control lines 158B–158E, similar to control line 158A.

In the embodiment illustrated, a silicon controlled rectifier (SCR) 180 is connected in series with the alternating current power source 164 so as to control power flow to each of the triacs 160, 170, 172, 174 and 176, and thus, to the respective heaters. The SCR 180 receives gate control signals from a triac 182. The triac 182 is also activated when a voltage potential on a control line 158F is lowered. The input buffer 162 also monitors the control line 158F.

The microprocessor 140 also receives input signals indicative of the operating temperatures of the heaters 98, 111, 113, 117, and those for oven 26. Suitable thermocouples are provided for each such heater, and provide signals indicative of heater temperature to a conditioner circuit 186 on signal lines 186A, 186B, 186C, 186D, and 186E, respectively. The conditioner circuit 186 includes suitable amplifiers and filters to condition the input signals received on signal lines 186A–186E. A signal line 187 couples the conditioner circuit 186 to an analog-to-digital converter 188 which, in turn, provides digital representations of the operating temperatures of the heaters to the microprocessor 140.

The microprocessor 140 initiates or controls any of the solenoid actuated valves 89, 90, 120 and the fan 102. The microprocessor 140 provides a control signal on a signal line 200 to a switch driver decoder indicated at 202 in FIG. 3B. The switch driver decoder 202 includes a plurality of output control lines 204, which in an "unselected" condition are at approximately 12 volts DC. An output control line 204A is lowered so as to activate the fan 102 by obtaining a suitable voltage potential across terminals of the fan 102. Optical coupler 206 is also activated so as to lower a potential voltage on an input data line 208A. The input data line 208A is coupled to an input buffer 210. The microprocessor 140 can access the input buffer 210 on a signal line 212 to ascertain if the control signal sent on signal line 200 was properly processed by the switch driver decoder 202 to lower the potential on the control line 204A. Voltages on control lines 204B, 204C and 204D are lowered and raised similar to control line 204A, described above, to initiate the solenoid actuated valves 89, 90 and 120, and simultaneously activate optical couplers 214, 216 and 218, respectively. The optical couplers 214, 216 and 218 control the voltage potential on signal lines 208B, 208C and 208D, respectively, in a manner similar to optical coupler 206.

The microprocessor 140 also verifies proper supply voltages are present in the fluid sampling system 10. Referring back to FIG. 3A, a power supply 230 receives electrical power from the alternating current power source 164. The power supply 230 transforms the alternating current electrical power to required DC voltage potentials used in the fluid sampling system 10. A voltage potential verification circuit is indicated generally at 232 and includes a plurality of optical couplers 236, 238, 240 and 242. Each optical coupler 236, 238, 240 and 242 is operably connected to one of the voltage potentials of the fluid sampling system 10. Using optical coupler 236 by way of example, when a voltage potential of −15 VDC is present, current flows through the optical coupler 236 so as to lower a voltage potential on an input data line 244A that is coupled to an input buffer 246. Other monitored system voltages activate the optical couplers 238, 240 and 242 to lower the voltage potential on input data lines 244B, 244C and 244D, respectively. The microprocessor 140 can access the input buffer 246 to ascertain if proper system voltages are present in the fluid sampling system 10.

Figure 4:
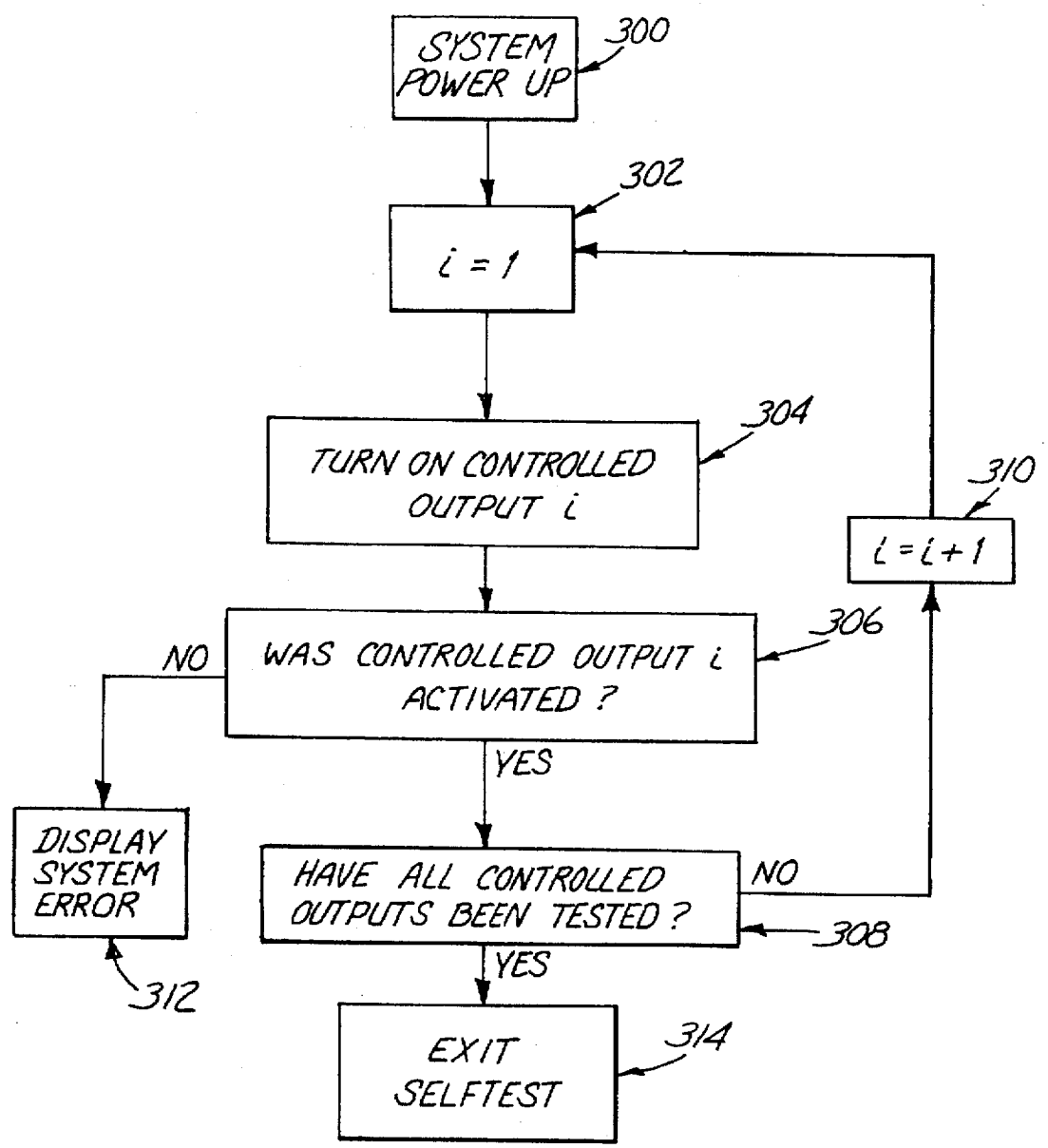
FIG. 4 is a flow diagram illustrating verification of controlled outputs.

A preferred method of monitoring the controlled devices (heaters 98, 111, 113, 117, and those in oven 26, the solenoid actuated valves 89, 90, 120, and the fan 102) is illustrated in the flow diagram of FIG. 4. Block 300 represents "system power up" when suitable power is supplied to the fluid sampling system 10. The microprocessor 140 then begins executing the program stored in memory 144 which includes initialization of an indicator pointer at block 302. At block 304, using the indicator pointer as a reference to the controlled devices of the fluid sampling system 10, the microprocessor 140 activates the first controlled device, for example, the heaters in oven 26, by providing a suitable control signal on signal line 154 as described above. Program flow then continues to block 306 whereat the input buffer 162 is accessed to ascertain if the control signal on signal line 154 was properly processed by the AC driver decoder 156. If the input buffer 162 verifies that the control signal on signal line 154 was properly processed, and if there remain additional controlled devices to be tested, as represented by block 308, program flow continues to block 310 whereat the indicator pointer is advanced.

Each of the controlled devices are tested according to the procedure outlined in blocks 304 and 306. If, in the event, one of the controlled devices does not respond upon testing, program flow advances to block 312 whereat a suitable error signal is displayed on the control panel 142 (FIG. 3A). Once all of the controlled devices have been tested (which can also include the system voltages), the microprocessor 140 exits the flow diagram of FIG. 4 at block 314. The microprocessor 140 then tests each of the heaters to verify the heater and the corresponding thermocouple are working. The microprocessor then begins execution of a suitable program to obtain samples from each of the canisters 12.

In the embodiment illustrated in FIGS. 3A–3B, verification of proper operation of the heaters 98, 111, 113, 117, and those in oven 26, was made by monitoring the control lines 158A–158E. It should be understood that other suitable sensing devices such as current transformers operably coupled to each of the power supply lines that provide electrical power to the heaters 26, 98, 11, 113 and 117 can also be used to verify that the heaters are operational. Although the thermocouples present in each of the heaters 26, 98, 111, 113 and 117 that provide signals back to the microprocessor 140 on signal lines 186A–186E can be used to verify proper operation of the heaters, response time is slower since the heaters must heat the thermal mass to which they are attached. By monitoring control signals in the manner described above, quick verification can be made that the control signals have been sent. It should be understood that other sensing devices such as Hall Effect switches and the like can be operably coupled to the solenoid actuated valves 89, 90, 120 or the fan 102, to verify proper operation of these devices.

Although the present invention has been described with respect to the fluid sampling system 10, it should be understood that the verification circuit can be incorporated in many types of fluid handling analytical instruments such as concentrators, autosamplers, headspace analyzers, and like analytical instruments. In addition, although the present invention has been described with reference to preferred embodiments, workers skilled in the art will recognize that changes may be made in form and detail without departing from the spirit and scope of the invention.

What is claimed is:

1. A fluid sampling system, comprising:
   a valve for controlling a sample taken from a sample enclosure, the valve having an inlet fluidly coupleable to receive such sample and an outlet;
   a controlled device;
   a controller operably coupled to the valve and the controlled device to selectively control the valve and the controlled device, wherein the controller provides a control signal to activate the controlled device; and
   a sensing device for sensing the control signal, the sensing device being coupled to the controller to provide a status signal indicative of activation of the controlled device.

2. The fluid sampling system of claim 1 wherein the controller comprises a computer.

3. The fluid sampling system of claim 2 wherein a control line couples the controller to the controlled device, and wherein the sensing device senses the control signal carried by the control line.

4. The fluid sampling system of claim 3 and further comprising an isolating switch coupled to the controller by the control line, the isolating switch controlling power to the controlled device.

5. The fluid sampling system of claim 1 and further comprising a second controlled device having terminals connectable to a source of electrical power and the sensing device senses a voltage potential across the terminals.

6. The fluid sampling system of claim 1 wherein controlled device receives power from a power source and the sensing device senses power flow to the controlled device.

7. The fluid sampling system of claim 1 wherein the controlled device comprises a heater and the sensing device includes a thermocouple measuring heat generated by the heater.

8. The fluid sampling system of claim 1 wherein the sample is gaseous.

9. A fluid sampling system, comprising:
   a valve for controlling a sample taken from a sample enclosure, the valve having an inlet fluidly coupleable to receive such sample and an outlet;
   a controlled device;
   a controller operably coupled to the valve and the controlled device to selectively control the valve and the controlled device; wherein a control line couples the controller to the controlled device; and
   a sensing device for sensing a control signal carried by the control line, the sensing device being coupled to the controller to provide a status signal indicative of activation of the controlled device.

10. The fluid sampling system of claim 9 wherein the sample is gaseous.

11. A fluid sampling system, comprising:
    a valve for controlling a sample taken from a sample enclosure, the valve having an inlet fluidly coupleable to receive such sample and an outlet;
    a controlled device having terminals connectable to a source of electrical power;
    a controller operably coupled to the valve and the controlled device to selectively control the valve and the controlled device; and
    a sensing device for sensing a voltage potential across the terminals indicating activation of the controlled device, the sensing device being coupled to the controller to provide a status signal indicative of activation of the controlled device.

12. The fluid sampling system of claim 11 wherein the sample is gaseous.

* * * * *